United States Patent [19]
Heinze

[11] Patent Number: 6,048,097
[45] Date of Patent: Apr. 11, 2000

[54] X-RAY EXAMINATION DEVICE WITH A C-ARM

[75] Inventor: Udo Heinze, Igensdorf, Germany

[73] Assignee: Siemens Aktiengesellschaft, Munich, Germany

[21] Appl. No.: 09/064,107

[22] Filed: Apr. 22, 1998

[30] Foreign Application Priority Data

Apr. 23, 1997 [DE] Germany ............................ 197 17 109
Feb. 3, 1998 [DE] Germany ............................ 198 04 178

[51] Int. Cl.$^7$ ...................................................... A61B 6/08
[52] U.S. Cl. ............................................ 378/206; 378/205
[58] Field of Search ..................................... 378/206, 205

[56] References Cited

U.S. PATENT DOCUMENTS 5,283,808 2/1994 Cramer et al. ........................... 378/206
5,583,909 12/1996 Hanover ................................... 378/197
5,690,107 11/1997 Hofmann .

FOREIGN PATENT DOCUMENTS 40 03 350 4/1991 Germany .
2 302 492 1/1997 United Kingdom .

Primary Examiner—David V. Bruce
Assistant Examiner—Michael J. Schwartz
Attorney, Agent, or Firm—Hill & Simpson

[57] ABSTRACT

In a stationary or mobile C-arm X-ray examination device with isocentric shifting of the C-arm, including rotation around a rotational axis, in order to enable an exact positioning of the patient, a light source is provided at the X-ray examination device which emits a light beam in the direction of the isocenter. For at least one position of the C-arm, the light beam and the rotational axis are assured to coincide, so that the projection of the light beam in a patient correctly identifies the isocenter.

7 Claims, 2 Drawing Sheets

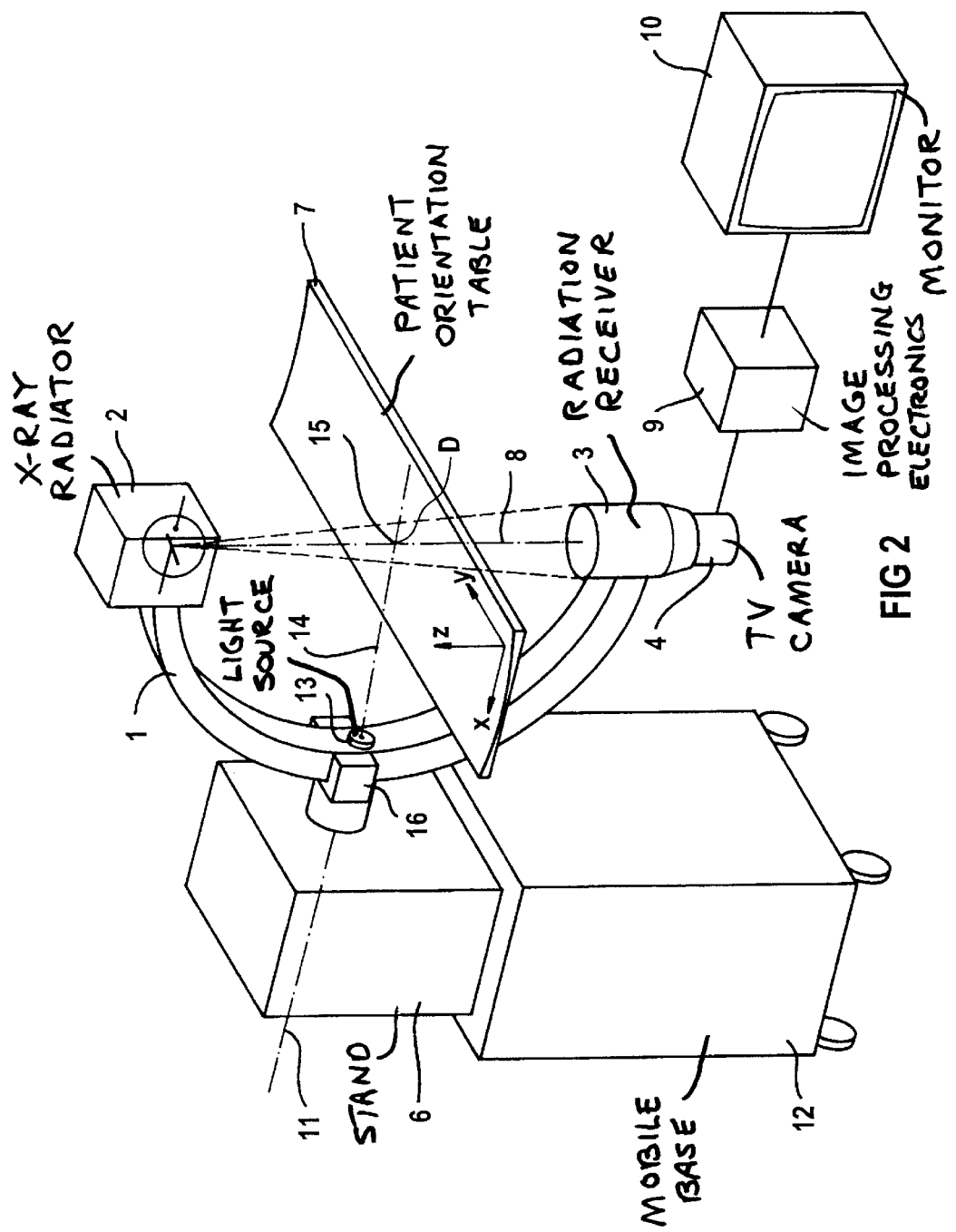

X-RAY EXAMINATION DEVICE WITH A C-ARM

BACKGROUND OF THE INVENTION

1. Field of the Invention

The present invention is directed to an X-ray examination device of the type having a C-arm which carries an X-ray radiator and a radiation receiver at its opposite ends, respectively.

2. Description of the Prior Art

Stationary and mobile X-ray examination devices are known which have a C-arm at whose ends an X-ray radiator and a radiation receiver are arranged, respectively. The C-arm is shiftable along its circumference in a circumferential direction and is rotatable around a horizontal axis, so that transirradiation of a patient oriented on a table is possible at different directions. The table is usually adjustable in three dimensions.

In such X-ray examination devices for the transillumination of a patient, it is problematic to arrange the X-ray radiator and the radiation receiver so that the patient's body region to be examined lies in the imaging field of the radiation receiver. German OS 295 09 546 (corresponding to United Kingdom Published Application 2 302 492) thus teaches the use of a laser light-beam localizer formerly two line lasers for the purpose of projecting a target cross onto the body surface of a patient. The line lasers are arranged at the X-ray radiator or the radiation receiver so that the center beam of an X-ray bundle emanating form the X-ray radiator proceeds along the lines of intersection of the two laser beams of the line lasers.

German OS 195 24 951 (corresponding to U.S. Pat. No. 5,690,107) teaches a computed tomography apparatus with a laser means for a similar purpose wherein, for example, in the preliminary stage of a tumor treatment of a patient by means of therapeutic radiation, the position and the extent of the tumor in the patient are detected in a diagnostic image produced with the computed tomography apparatus. Once the tumor's position and size are thus determined, a projection with the aid of line lasers of the laser means is made onto the body surface of the patient for marking, in order to enable a reproducible positioning of the patient relative to the therapeutic radiation means.

For simplifying the examination of a patient, in a C-arm X-ray device of the type previously described, an isocenter can be identified which is characterized by the center beam of an X-ray bundle emanating form the X-ray radiator always running through the center of rotation of the C-arm, so that different projections can be performed without a repositioning of the patient relative to the C-arm. If the subject of interest in the patient is in the isocenter before a shifting of the C-arm, then this subject does not wander out of the isocenter given an orbital motion and given an angling motion of the C-arm, since this isocenter always remains in the same point in space, independently of the orbital and angling motions, as long as the C-arm is not shifted vertically or horizontally. In mobile X-ray examination devices, however, the table generally is independent of the C-arm device. Even if, given shifting of the C-arm, the isocenter of the mobile C-arm device does not change with reference to its spatial position, the examination object can wander out of the imaging area if the table position changes. It is therefore desirable to be able to check the spatial position of the isocenter.

German PS 40 03 350 teaches a C-arm device with an isocentrically shiftable C-arm which is provided with two lasers whose beams cross in the isocenter of the C-arm and thus characterize the position of the isocenter.

It has proved to be disadvantageous, however, to position a patient relative to the C-arm device in this way, because the isocenter is located in the body of the patient. Two laser points are projected onto the body surface of the patient from different directive without a visible intersection, and thus the position of the isocenter is not clearly identifiable.

Beyond this, the lasers are arranged at the C-arm in such a way that the laser points wander—particularly around the angling axis of the C-arm—given angling movements of the C-arm over the body surface of the patient, so that precise identification of the spatial position of the isocenter is further impeded.

SUMMARY OF THE INVENTION

It is an object of the present invention to provide an X-ray examination device with a C-arm wherein the spatial position of the isocenter of the C-arm can be checked easily without using X-ray radiation, even given angling motions of the C-arm.

The object is inventively achieved in an X-ray examination device with a C-arm at whose ends an X-ray radiator and an imaging system are respectively arranged, this C-arm being shiftable along its circumferential direction and being supported so that it is rotatable around a horizontal axis, with the shifting of the C-arm ensuing so that the center beam of the X-ray radiator always runs through the isocenter of the C-arm, and wherein a light source which emits a light beam running through the isocenter is arranged at the X-ray device so that the path of the light beam of the light source substantially coincides with the axis in at least one position of the C-arm. Because of this, in at least one position of the C-arm, which is preferably the position in which the center beam of the X-ray radiator runs vertically, a point of light projected onto the body surface of the patient by means of the light source always remains in the same place on the body surface, given angling motions of the C-arm about the axle, and thus permits a clear checking of the spatial position of the isocenter for angling movements of the C-arm in an advantageous manner.

In an embodiment of the invention that the C-arm is supported in a holder at which the light source is arranged such that the path of the light beam of the light source substantially coincides with the axis independently of the position of the C-arm. Because of this, the point of light of the light source which is projected onto the body surface of a patient always remains in substantially the same place on the body surface of the patient, not only given orbital motions, but also given angling motions of the C-arm, and permits a clear identification of the spatial position of the isocenter.

In another embodiment of the invention the light source is arranged at the C-arm. The light source can be arranged for example in the middle of the C-arm, the "middle" being characterized by the plane which divides the C-arm into two nearly identical C-arm segments in the shape of quarter-rings. In this way, given angling motions of the C-arm around the axis, the point of light of the light source which is projected onto the body surface of a patient always remains in substantially the same place on the body surface of the patient and enables a clear identification of the spatial position of the isocenter, at least in the most commonly used position of the C-arm, wherein the center beam of the X-ray radiator runs vertically.

The light source can be a point-laser which, due to the tightly bundled light, is particularly suited to the identification of the spatial position of the isocenter.

The X-ray examination device can be configured in a mobile manner so that the X-ray examination device can be used independent of its location.

DESCRIPTION OF THE DRAWINGS

FIG. 2 shows a C-arm X-ray device constructed in accordance with the invention, wherein the light source is arranged in the middle of the C-arm.

DESCRIPTION OF THE PREFERRED EMBODIMENTS

Figure 1:
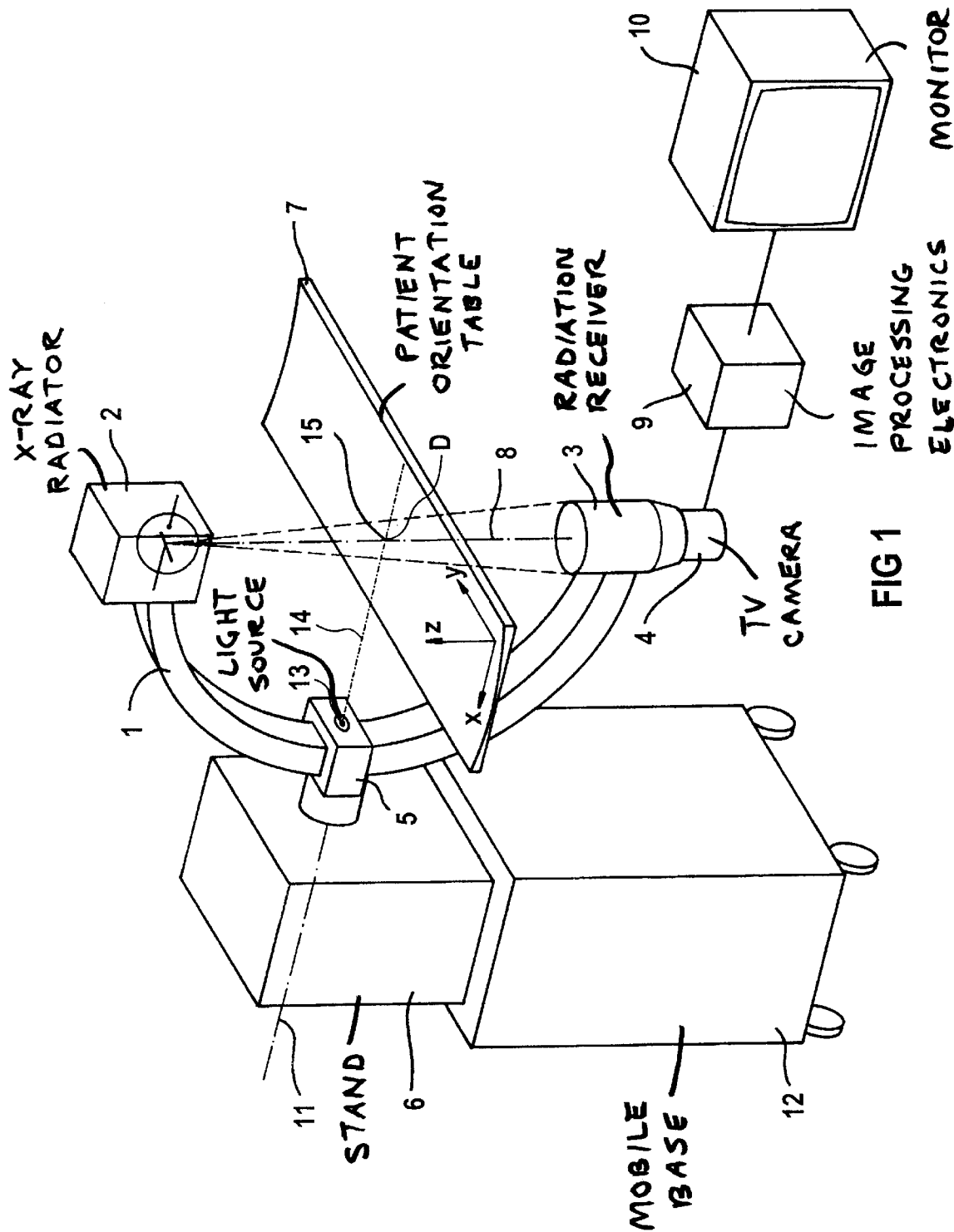
FIG. 1 shows a C-arm X-ray device constructed in accordance with the invention, wherein the light source is arranged at the holder of the C-arm.

FIG. 1 depicts a mobile X-ray examination device with a C-arm 1, this device carrying an X-ray radiator 2 at its one end and an X-ray image intensifier 3 at the other end, to whose luminescent output screen a TV camera 4 is optically coupled. The C-arm 1 is supported in a holder 5 so that it can be shifted along its circumferential direction, this holder 5 being secured at a stand 6. The C-arm 1 is rotatable together with the holder 5 around a horizontally running axis 11 relative to the stand 6. The stand 6 is supported on a mobile base 12 so that it can be adjusted in height. The patient (not shown in the figures) is oriented on a patient orientation table 7 which is spatially adjustable in three dimensions. The center beam of an X-ray bundle emanating form the X-ray radiator 2 is designated 8 and constantly runs through the center of rotation D of the C-arm 1, which point corresponds to the isocenter 15 of the C-arm 1, so that the orbital and angling motions of the C-arm 1 ensue isocentrically. The X-ray image picked up by the TV camera 4 is reproduced on a monitor 10 via known image processing electronics 9.

A light source in the form of a point laser 13 is arranged at the holder 5, this point laser emitting a laser beam 14 which is directed onto the isocenter 15 of the X-ray examination device and which coincides with the axis 11; i.e., the path of the laser beam 14 and the path of the axis 11 are identical in the case of the present exemplary embodiment. The shifting of the C-arm 1 in the circumferential direction and its rotation about the axis 11 (orbital and angling motions) ensues in such a way that, in stationary X-ray examination devices, the spatial position of the isocenter 15 does not change given the shifting of the C-arm 1. Therefore, with the aid of the laser beam 14, the position of the isocenter 15 can be projected in the form of a laser point (not further depicted) onto the body surface of the patient oriented on the patient (not shown) orientation table 7.

It is advantageous that the path of the axis 11 and the path of the laser beam 14 of the point-laser 13 are identical, since, in this way, independently of orbital or angling motions of the C-arm 1, i.e. independently of the position of the C-arm 1, the laser point of the laser beam 14 projected on the body surface of the patient remains constantly in the same place on the body surface of the patient, and therefore constantly correctly characterizes the spatial position of the isocenter 15.

FIG. 2 shows a further exemplary embodiment of the inventive X-ray examination device, which is largely identical to the X-ray examination device shown in FIG. 1, so that like components are provided with like reference characters.

In contrast to the X-ray examination device depicted in FIG. 1, the X-ray examination device in FIG. 2 has a modified holder 16 for the C-arm 1. As in the case of the exemplary embodiment in FIG. 2, the holder 16 serves to support of the C-arm 1 for shifting motions of the C-arm 1 in the circumferential direction. The holder 16 is, however, open at the side facing the patient orientation table 7, i.e. it is of a U-shaped form.

In the case of the exemplary embodiment depicted in FIG. 2, the light source is arranged in the form of a point laser 13 in the middle of the C-arm 1. The point-laser 13 in turn emits a laser beam 14 which is directed onto the isocenter 15 of the X-ray examination device. As in the previously described exemplary embodiment of FIG. 1, the shifting of the C-arm 1 in the circumferential direction and its rotation about the axis 11 ensue in such a way that, in the shifting of the C-arm 1, the spatial position of the isocenter 15 does not change in stationary X-ray examination devices. With the aid of the laser beam 14, the position of the isocenter 15 can therefore be projected onto the patient (not shown) oriented on the patient orientation table 7.

If, during X-ray examinations of a patient, the C-arm 1 is located in the position depicted in FIG. 2, in which the center beam 8 of an X-ray bundle emanating from the X-ray radiator 2 runs vertically, then the laser point of the laser beam 14 projected on the body surface of the patient advantageously remains constantly in the same place on the body surface of the patient given angling movement of the C-arm 1 about the axis 11, correctly characterizing the spatial position of the isocenter 15. The path of the laser beam 14 substantially coincides with the path of the axis 11.

In the case of the exemplary embodiment depicted in FIG. 2, the light source 13 need not necessarily be alternatively arranged in the middle of the C-arm 1, but can also be arranged in another position of the C-arm 1 if appropriate.

Moreover, the X-ray examination device need not necessarily be mobile, and the light source need not be a point laser.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray examination device comprising:

a C-arm having first and second opposite ends and a circumference extending between said first and second opposite ends, said C-arm having an isocenter associated therewith;

an X-ray radiator mounted at the first end of said C-arm, said X-ray radiator emitting an X-ray beam bundle including a center X-ray beam;

a radiation receiver, on which said X-ray beam bundle is incident, mounted at said second end of said C-arm;

means for mounting said C-arm for moving said C-arm along said circumference for causing said center X-ray beam always to proceed through said isocenter of said C-arm, and for rotating said C-arm around a horizontal axis; and a light source mounted relative to said C-arm which emits a light beam having a path proceeding through said isocenter and said path of said light beam substantially coinciding with said axis in at least one position of said C-arm, and, said light beam not coinciding with said center X-ray beam.

2. An X-ray examination device as claimed in claim 1 wherein said means for mounting said C-arm comprises a holder and wherein said light source is mounted on said holder so that said path of said light beam substantially coincides with said axis independently of any position of said C-arm.

3. An X-ray examination device as claimed in claim 1 wherein said light source is mounted on said C-arm.

4. An X-ray examination device as claimed in claim 3 wherein said light source is mounted in a middle of said circumference of said C-arm between said first and second ends.

5. An X-ray examination device as claimed in claim 1 wherein said light source comprises a point laser.

6. An X-ray examination device as claimed in claim 1 wherein said means for mounting said C-arm comprises a mobile unit.

7. An X-ray examination device as claimed in claim 1 further comprising an imaging system, including means for displaying an image of a subject irradiated by said X-ray beam bundle, optically coupled to said radiation receiver.

* * * * *